(12) United States Patent
Eich et al.

(10) Patent No.: US 12,318,586 B2
(45) Date of Patent: Jun. 3, 2025

(54) DUAL-FUNCTION SPRING

(71) Applicant: Ypsomed AG, Burgdorf (CH)

(72) Inventors: Adrian Eich, Wangenried (CH); Aurèle Horisberger, Allschwil (CH); Patrick Hostettler, Hasle-Rüegsau (CH); Malte Kladiwa, Bern (CH); Stefan Meier, Aarberg (CH); Peter Stettler, Kirchberg (CH); Jürgen Wittmann, Burgdorf (CH)

(73) Assignee: Ypsomed AG, Burgdorf (CH)

( * ) Notice: Subject to any disclaimer, the term of this patent is extended or adjusted under 35 U.S.C. 154(b) by 0 days.

(21) Appl. No.: 18/295,160

(22) Filed: Apr. 3, 2023

(65) Prior Publication Data

US 2023/0277771 A1  Sep. 7, 2023

Related U.S. Application Data

(63) Continuation of application No. 16/441,954, filed on Jun. 14, 2019, now abandoned, which is a
(Continued)

(30) Foreign Application Priority Data

Feb. 29, 2008  (DE) ............... 10 2008 011 885.0

(51) Int. Cl.
*A61M 5/24* (2006.01)
*A61M 5/315* (2006.01)
(Continued)

(52) U.S. Cl.
CPC ............ *A61M 5/24* (2013.01); *A61M 5/2422* (2013.01); *A61M 5/31511* (2013.01);
(Continued)

(58) Field of Classification Search
CPC .. A61M 2005/2006; A61M 2005/2073; A61M 2005/2403; A61M 2005/2411;
(Continued)

(56) References Cited

U.S. PATENT DOCUMENTS 5,279,586 A  1/1994  Balkwill
5,480,390 A  1/1996  Hajishoreh
(Continued)

FOREIGN PATENT DOCUMENTS

EP  0554995 A1  8/1993
WO  0041754 A1  7/2000
(Continued)

OTHER PUBLICATIONS

PCT , "International Preliminary Report on Patentability", Application No. PCT/CH2009/000078, Sep. 21, 2010, 13 pages.
(Continued)

*Primary Examiner* — Shefali D Patel
(74) *Attorney, Agent, or Firm* — Dorsey & Whitney LLP

(57) ABSTRACT

An injection device for dispensing a product, the injection device including a moveable element which is moved for a dispensing operation, a spring, a product container holder and a product container, wherein the spring pushes against the moveable element to move the moveable element to an initial position after the dispensing operation has ended and against the product container to seat the product container in the product container holder.

10 Claims, 11 Drawing Sheets

Related U.S. Application Data continuation of application No. 15/043,998, filed on Feb. 15, 2016, now abandoned, which is a continuation of application No. 14/612,450, filed on Feb. 3, 2015, now abandoned, which is a continuation of application No. 12/869,362, filed on Aug. 26, 2010, now Pat. No. 8,992,487, which is a continuation of application No. PCT/CH2009/000078, filed on Feb. 26, 2009.

(51) Int. Cl.
*A61M 5/20* (2006.01)
*A61M 5/31* (2006.01)

(52) U.S. Cl.
CPC ........... *A61M 5/31543* (2013.01); *A61M 5/20* (2013.01); *A61M 2005/202* (2013.01); *A61M 2005/2086* (2013.01); *A61M 2005/2403* (2013.01); *A61M 2005/2407* (2013.01); *A61M 2005/2433* (2013.01); *A61M 2005/244* (2013.01); *A61M 2005/2477* (2013.01); *A61M 2005/2481* (2013.01); *A61M 2005/2488* (2013.01); *A61M 5/3129* (2013.01); *A61M 5/31541* (2013.01); *A61M 5/31553* (2013.01); *A61M 5/31558* (2013.01); *A61M 5/31561* (2013.01); *A61M 5/31583* (2013.01)

(58) Field of Classification Search
CPC .. A61M 2005/2433; A61M 2005/3125; A61M 2005/3126; A61M 2005/31508; A61M 5/20; A61M 5/24; A61M 5/2422; A61M 5/3129; A61M 5/315; A61M 5/31501; A61M 5/31511; A61M 5/31515; A61M 5/31525; A61M 5/31528; A61M 5/31533; A61M 5/31535; A61M 5/31541; A61M 5/31545; A61M 5/31548; A61M 5/3155; A61M 5/31551; A61M 5/31553; A61M 5/31563; A61M 5/31565; A61M 5/31566; A61M 5/31571; A61M 5/31576; A61M 5/31578; A61M 5/3158; A61M 5/31583; A61M 5/31585; A61M 5/3159; A61M 5/31543

See application file for complete search history.

(56) References Cited

U.S. PATENT DOCUMENTS

| | | | |
|---|---|---|---|
| 6,221,046 B1* | 4/2001 | Burroughs | A61M 5/31551 604/207 |
| 6,235,004 B1* | 5/2001 | Steenfeldt-Jensen | A61M 5/31551 604/207 |
| 2004/0236285 A1 | 11/2004 | Fisher et al. | |
| 2005/0137571 A1 | 6/2005 | Hommann | |
| 2007/0005021 A1 | 1/2007 | Kohlbrenner et al. | |
| 2007/0021718 A1 | 1/2007 | Burren et al. | |
| 2009/0137966 A1 | 5/2009 | Rueckert et al. | |
| 2009/0254035 A1 | 10/2009 | Kohlbrenner et al. | |
| 2016/0158445 A1 | 6/2016 | Eich et al. | |
| 2019/0290851 A1 | 9/2019 | Eich et al. | |

FOREIGN PATENT DOCUMENTS

| | | |
|---|---|---|
| WO | 2004002557 A1 | 1/2004 |
| WO | 2008031239 A1 | 3/2008 |

OTHER PUBLICATIONS

PCT , "International Search Report and Written Opinion", Application No. PCT/CH2009/000078, Jul. 6, 2009, 18 pages.

* cited by examiner

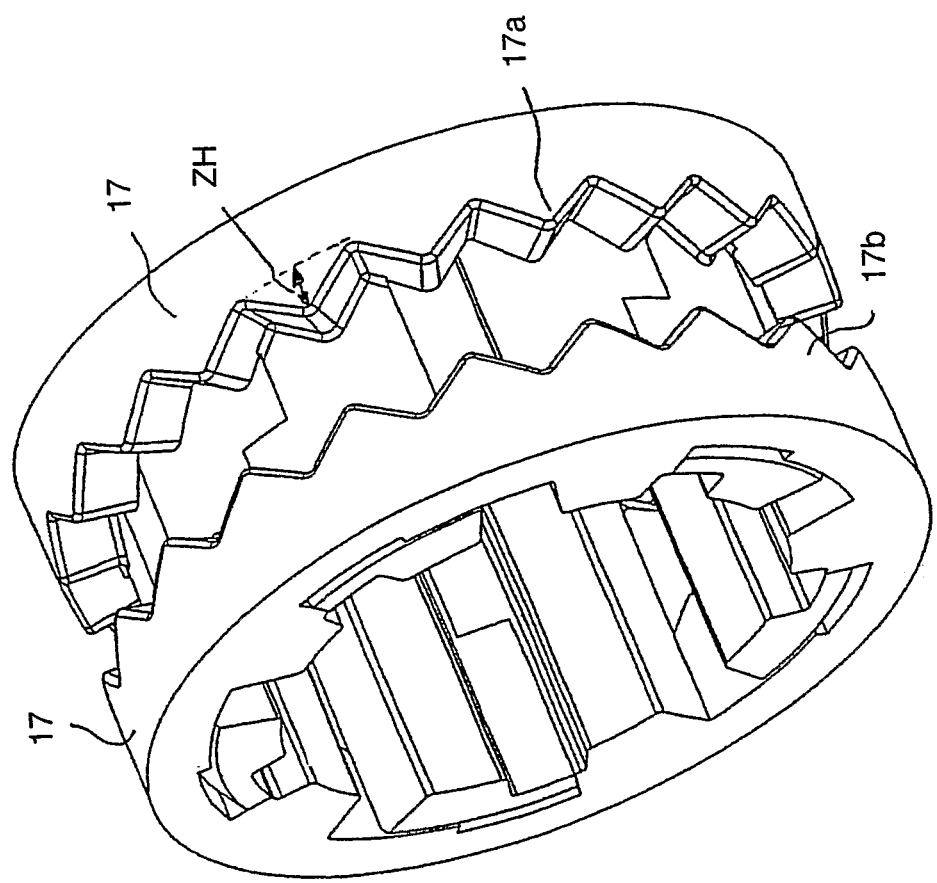

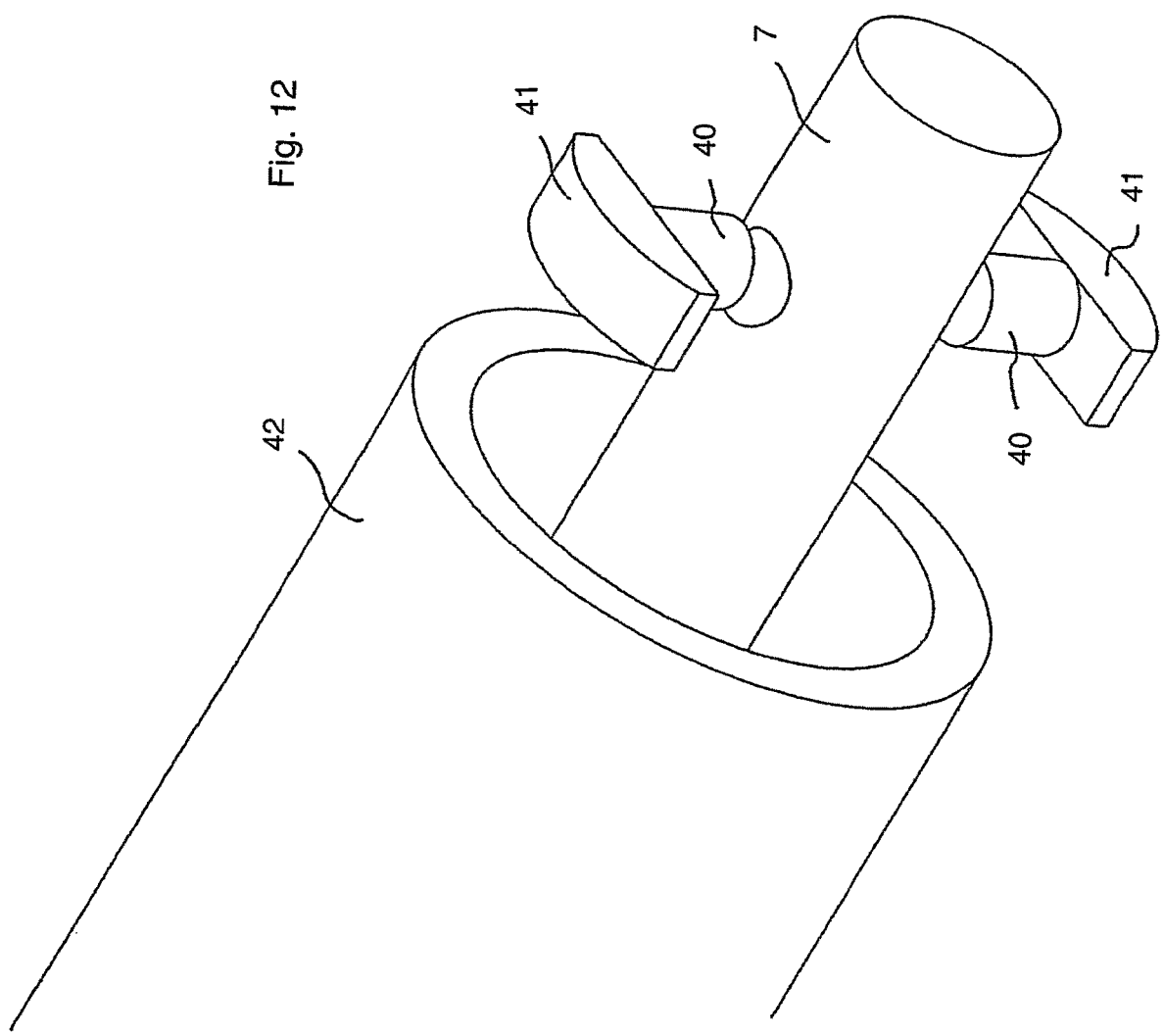

DUAL-FUNCTION SPRING

CROSS-REFERENCE TO RELATED APPLICATIONS

This application is a continuation of U.S. application Ser. No. 16/441,954, filed on Jun. 14, 2019, which is a continuation of U.S. application Ser. No. 15/043,998, filed Feb. 15, 2016, which is a continuation of U.S. application Ser. No. 14/612,450, filed Feb. 3, 2015, which is a continuation of U.S. application Ser. No. 12/869,362, filed Aug. 26, 2010, issued as U.S. Pat. No. 8,992,487 on Mar. 31, 2015, which is a continuation of International Patent Application No. PCT/CH2009/000078 filed Feb. 26, 2009, which claims priority to German Patent Application No. 10 2008 011 885.0 filed Feb. 29, 2008, the entire contents of each of which are incorporated herein by reference.

BACKGROUND

The present invention related to devices for injecting, infusing, administering, dispensing or delivering a substance, and to methods of making and using such devices. More particularly, the present invention relates to an injection device for administering a substance or product such as a medicament or therapeutic substance, e.g. insulin, growth hormone, etc.

The idea of coupling an ampoule (which also may be referred to and/or thought of as a container, carpoule, vial or the like) containing a product to or in an injection device is known from the prior art. Securing an ampoule in a stationary seating, for example in an ampoule holder, when attached to the injection device is also known. In some cases, the ampoule may be screwed into the holder, and the securing or holding may be achieved by a clamping action wherein the product container accommodated in the ampoule holder is clamped between the distal (forward) end of the ampoule holder and a stop which acts on the distal end of the ampoule.

SUMMARY

An object of the present invention is to provide an injection device to which a product container can be secured in a reliable, efficient and economic manner.

In one embodiment, the present invention comprises an injection device for dispensing a product, the injection device including a moveable element which is moved for a dispensing operation, a spring, a product container holder and a product container, wherein the spring pushes against the moveable element to move the moveable element to an initial position after the dispensing operation has ended and against the product container to seat the product container in the product container holder.

In one embodiment of an injection device according to the present invention, the device comprises coupling element, a product container, and a spring between the coupling element and the product container, the spring biasing or urging the coupling element in one direction and the product container in the other, i.e. opposite, direction.

In some embodiments, the present invention comprises an injection device whereby an injection may be administered manually by the user or may take place automatically. For example, a user of an embodiment of the device designed for automatically dispensing the product may operate an operating element which releases a drive element, for example a spring, and the spring force acts indirectly or directly on an output element and/or pushes the plunger of a product container in a dispensing direction. The drive element may be a motor, a pyrotechnic propellant charge or, as in some preferred embodiments of the present invention, a spring, e.g. a mechanical spring. If the drive element is of the type which stores energy, in some preferred embodiments the stored energy can be released by an operating element so that a driving movement can be converted into an output movement. In some embodiments, the driving movement may be a rotating movement, and the output movement may be a linear movement.

In some preferred embodiments, the drive element may be a rotating spring, e.g. a helical or clock spring, which is wound about the longitudinal axis of the injection device. For example, the spring may be supported in a fixed arrangement on the housing in at least one direction of rotation by one end and connected to the output element or a part which is or can be coupled with the output element by the other end. Thus, the rotational energy stored in the spring may be converted into a driving movement. In some embodiments, it is advantageous to use a strip-shaped helical spring.

In some embodiments, an injection device in accordance with the present invention may be disposable. Generally, in such embodiments, a product container inserted or built into the device during production can not be replaced, and when empty or after the injection device has been used, it is disposed of as a whole together with the product container.

In some embodiments, an injection device in accordance with the present invention is designed to be used more than once. This is practical if the injection device is fitted with high-quality and/or high-tolerance components designed to make it easy to dispense a product and which may be too expensive for use with disposable items. In some embodiments, a driving mechanism is incorporated in a drive unit, in which case the product container can be attached to the drive unit, and can be detached from the drive unit. An empty product container can be released from the drive unit, disposed of and replaced by a new one.

In some preferred embodiments, the product container is received and/or seated in a product container holder. The product container holder is sleeve-shaped and has an opening through which the product container can be inserted into the interior of the sleeve. The opening may be disposed laterally or on an end, e.g. the proximal (rear) end, of the product container holder. At the side, the product container holder may have a region through which it is possible to see from the outside into the interior of the container holder to, for example, ascertain whether a product container has been inserted or to check how full an inserted product container is. The product container holder may have a collar at its distal (forward) end, against which the product container sits in an abutting contact in its inserted state. The product container is then fixedly seated in the product container holder. The product container holder may have a conical shape, and the product container can be pushed into it to obtain a fixed seating.

In some preferred embodiments, an injection device in accordance with the present invention, e.g. the drive unit thereof, may comprise a spring element, such as a mechanical spring, a gas compression spring or other elastic means, which acts on or pushes on the product container, e.g. the part of the product container relative to which the plunger can be displaced. In some preferred embodiments, the spring element may push the product container into a fixed seating with and/or within the product container holder. In some preferred embodiments, the spring element may act in the longitudinal direction of the injection device.

In some embodiments of the present invention, the product container may be an ampoule or capped vial, for example, and is open at its proximal (rear) end and closed at its distal (forward or front) end. An output element of the drive unit may extend through the proximal end into the product container to act on a plunger or piston in the container, which plunger or piston can be displaced relative to the product container wall. The distal end may incorporate or carry a needle, or may be designed so that a needle can be attached, thereby establishing a flow connection to the interior of the product container due to the fact that the needle pierces a septum disposed on the distal end of the product container. In some preferred embodiments, the wall of the product container is cylindrical, and it may be tightly enclosed by the sleeve-shaped product container holder or enclosed with a slight clearance.

In some embodiments, the injection device may have an element which is moved back into an initial position after a dispensing operation has ended or as it is ending. This may be an operating element which can be operated by moving it, e.g. by moving it axially along a longitudinal axis of the injection device. The element may be moved into a dispensing position as the dispensing operation is being actuated or triggered, in which case the direction of movement needed for this purpose is opposite the direction of movement in which the element can move on terminating the dispensing operation. The operating element may be operated by a user of the device to trigger and/or stop dispensing of the product, or it may be released after the product has been dispensed whereby it moves back or automatically returns to its initial position. A lock element may be coupled with the operating element so that it is axially locked, at least in one direction and, in some preferred embodiments, in both directions.

In some embodiments, the operating element moves back or can be moved back to an initial position after the dispensing operation has terminated. Thus, an injection device in accordance with the present invention may comprise a coupling, e.g. a coupling element which establishes or releases a coupling as it is moved. For example, such a coupling element may be coupled with the operating element in at least one direction and at least for a certain time. The coupling element may push the operating element in one direction, and in the other, opposite direction, the operating element may push the coupling element.

In some preferred embodiments, the element which is moveable when a dispensing operation is terminated or triggered may be moved back into an initial position by a spring element when the dispensing operation has terminated. The spring element may also urge the product container into its fixed seating. In some preferred embodiments, the spring element is a helical spring, which may be wound from a wire-like material. The spring element may be disposed parallel and/or concentrically with the longitudinal axis of the injection device.

In some preferred embodiments, a spring in accordance with the present invention may fulfil a dual function, namely that of pushing the product container into its fixed seating and that of providing the requisite force for the element which moves back to an initial position when a dispensing operation has terminated. An advantage of using a spring to urge or push the product container into its fixed seat or location is that it offers an easy way of compensating for variations in the longitudinal tolerances of product containers. It also allows an injection device to be used with product containers produced by different manufacturers. Another advantage of using a spring with a dual function is that it may replace or avoid the use of two separate springs, one of which pushes the product container and the other of which pushes the operating element, thereby reducing costs.

In some embodiments, the element which can be moved back to its initial position after the dispensing operation has terminated may prevent, e.g. lock, a movement of the output element relative to the housing when it is in a coupled state and unlock, i.e. release it, relative to the housing when it is in an uncoupled state. In some preferred embodiments, this locking effect is provided by an anti-rotation lock. In some preferred embodiments, to effect a dispensing operation, the moveable element, which may be a part of a coupling, is moved out of the coupled engagement for a dispensing operation. To this end, it may be moved out of the coupled engagement by the operating element, in which case the operating element is operated, e.g. pushed, as a result of which the element is moved out of the coupled engagement against the spring force of the spring element. The element may be able to be moved axially relative to a housing and/or the drive unit of the injection device, but not rotate. The dispensing movement of the output element, which may be a plunger rod and have a freely rotatable but axially fixed flange on its end, can be effected relative to the housing or a locating element which moves into or is positioned in the output element. In some embodiments, the locating element may locate in (or be received in or coupled to) the output element so that the output element can be moved axially relative to the locating element in and/or opposite the dispensing direction, e.g. turned or screwed. For example, the locating element may have an internal thread which locates in and/or complements an external thread of the output element. Alternatively, the output element may be longitudinally guided by the locating element. The locating element may be secured so that it is not able to rotate relative to the housing and may also be secured so that it can not move axially, although this is not necessarily the case. In some preferred embodiments, the locating element is able to move axially relative to the housing, in which case it is secured to the housing so that it can not move axially when a product container has been inserted and secured on the drive unit.

In some preferred embodiments, the output element which acts on the product to be dispensed to dispense the product, e.g. via the plunger, is coupled with the re-settable element in such a way that its dispensing movement is locked when the product container is not attached. This means that triggering is not possible if a product container has not been inserted.

In some preferred embodiments, the output element is unlocked and can effect a rotating movement in the state in which a product container has not been inserted so that the output element can be screwed back, e.g. in the proximal direction, by a rotating movement of the output element into the drive unit if a product container has not been inserted or if a product container holder has been removed. In some preferred embodiments, the thread by which the locating element locates in the output element has a pitch which does not cause any frictional resistance of the thread when placed under axial load. When pressure is applied to the output element, e.g. to the flange thereof, in the proximal direction, it is able to move easily in the proximal direction without the user having to apply a rotating movement to the output element. If a product container has been removed or if a product container holder has been removed, the locating element can be moved between a first position and a second position, and in the first position, the output element is uncoupled from the element so that the output element is able to move in or opposite the dispensing direction. Providing the product container or the product container holder has been attached to the drive unit, the locating element is moved into its second position, thereby preventing a rotating movement of the output element. For example, the locating element may be moved by the product container or by the product container holder directly or indirectly, for example by the fixing device. The product container or the product container holder may constitute or incorporate a part of the fixing device. A movement out of an unsecured state into the secured state, e.g. a rotating movement of the product container or product container holder, in some preferred embodiments, a combined rotating-axial movement, causes the locating element to move.

In some preferred embodiments, the locating element is coupled with the fixing device so that when the product container or product container holder is attached or released, it is moved axially on or by the drive unit. The locating element may be connected in an axially fixed arrangement to a coupling element, such as a coupling sleeve, which is in turn able to rotate relative to the locating element. The coupling element may be sleeve-shaped and surround the output element or at least cooperate with the output element so that the output element is able to move axially relative to the coupling element but not rotate. The coupling element may locate in a longitudinal groove of the output element. The coupling element may be part of a transmission which transmits the torque of the drive element to the output element. Another element may be connected to the drive element in a fixed torque-transmitting arrangement, such as a drive shaft which is or can be coupled with the output element, due to the fact that the drive shaft can be coupled with the output element via a coupling which can be axially engaged with and released from the output element. To this end, the coupling element and the drive shaft may form part of the coupling, which can be coupled and uncoupled.

In some embodiments, the coupling element may also have projections, which are moved into engagement or out of engagement with the re-settable element depending on the desired operating mode.

In some preferred embodiments, the spring element fulfilling the dual function is disposed between a re-settable element and the product container. It may be advantageous if the re-settable element is subjected to a force acting in the proximal (rearward) direction by the spring and the product container is subjected to a force acting in the distal (forward) direction by the spring. The spring element may act directly or indirectly on the product container. In some preferred embodiments, the spring acts via one or more parts disposed between the product container and the spring element. For example, a retainer or retaining element may be disposed between the product container and spring element, which pushes on the proximal end of the product container by its distal end. The retaining element may have an axial stop which prevents the spring element from fully relaxing when a product container is being removed or has been removed. For example, the stop may move into an abutting contact with the locating element so that the retaining element is moved axially by a distance which is limited but long enough to compensate for longitudinal tolerances of the product container. The retaining element may be displaceable relative to the locating element and/or to the housing. The arrangement may be such that the spring expends a force on the re-settable element and also on the operating element for example, when a product container is inserted.

In some embodiments, one or more parts, e.g. at least one other part, may be provided between the spring and operating element, in addition to the re-settable element, which can be moved by the operating element and/or by the element which is re-settable by the spring element. For example, a bearing may be provided between the operating element and the re-settable element, which provides a bearing for the coupling element transversely to the longitudinal direction, and/or a threaded sleeve which can be used to produce a rotating movement for additional parts of the injection device, e.g. a dose display or a dose stop for the final dose, and/or a brake to restrict the driving speed, and/or a drive element which supplies the driving energy needed to dispense the product. These parts may be moved in the distal direction when the operating element is operated, for example, and in the proximal direction during the re-setting movement of the spring element. This being the case, the spring element also fulfils the function of holding together axially adjoining parts or components. In some embodiments, the spring element may also be used to couple and uncouple various couplings, i.e. supply coupling forces.

In some embodiments, the spring fulfilling the dual function may be a separate part or component, or it may be a part formed by a structure or element adjoining the spring. If a separate spring is provided, it may be made from a suitable material, e.g. plastic, metal, etc. In some embodiments, if the spring is an integral part of another component, the spring may be made from plastic because it can be injection molded with the other part. An advantage of this is that it may be possible to reduce costs. Alternatively, in using a metal spring, the element which the spring is part of can be cast around it. This may be done by a simple injection casting process. For example, the spring may be integral with the re-settable element or integral with a supporting ring which may be provided as a separate part between the spring and retaining element, or integral with the retaining element which pushes on the product container and/or comprises an axial stop. Another option is for the retaining element, spring and re-settable element to be of an integral design.

BRIEF DESCRIPTION OF THE DRAWINGS

FIGS. 7A and 7B are, respectively, an exploded diagram and a perspective view of one embodiment of a brake mechanism in accordance with the present invention, FIG. 12 is a perspective view of another embodiment of a brake mechanism in accordance with the present invention operating on the principle of a centrifugal brake.

DETAILED DESCRIPTION

With regard to fastening, mounting, attaching or connecting components of the present invention, unless specifically described as otherwise, conventional mechanical fasteners and methods may be used. Other appropriate fastening or attachment methods include adhesives, welding and soldering, the latter particularly with regard to the electrical system of the invention, if any. In embodiments with electrical features or components, suitable electrical components and circuitry, wires, wireless components, chips, boards, microprocessors, inputs, outputs, displays, control components, etc. may be used. Generally, unless otherwise indicated, the materials for making embodiments of the invention and/or components thereof may be selected from appropriate materials such as metal, metallic alloys, ceramics, plastics, etc. Unless otherwise indicated specifically or by context, positional terms (e.g., up, down, front, rear, distal, proximal, etc.) are descriptive not limiting. Same reference numbers are used to denote same parts or components.

Figure 1:
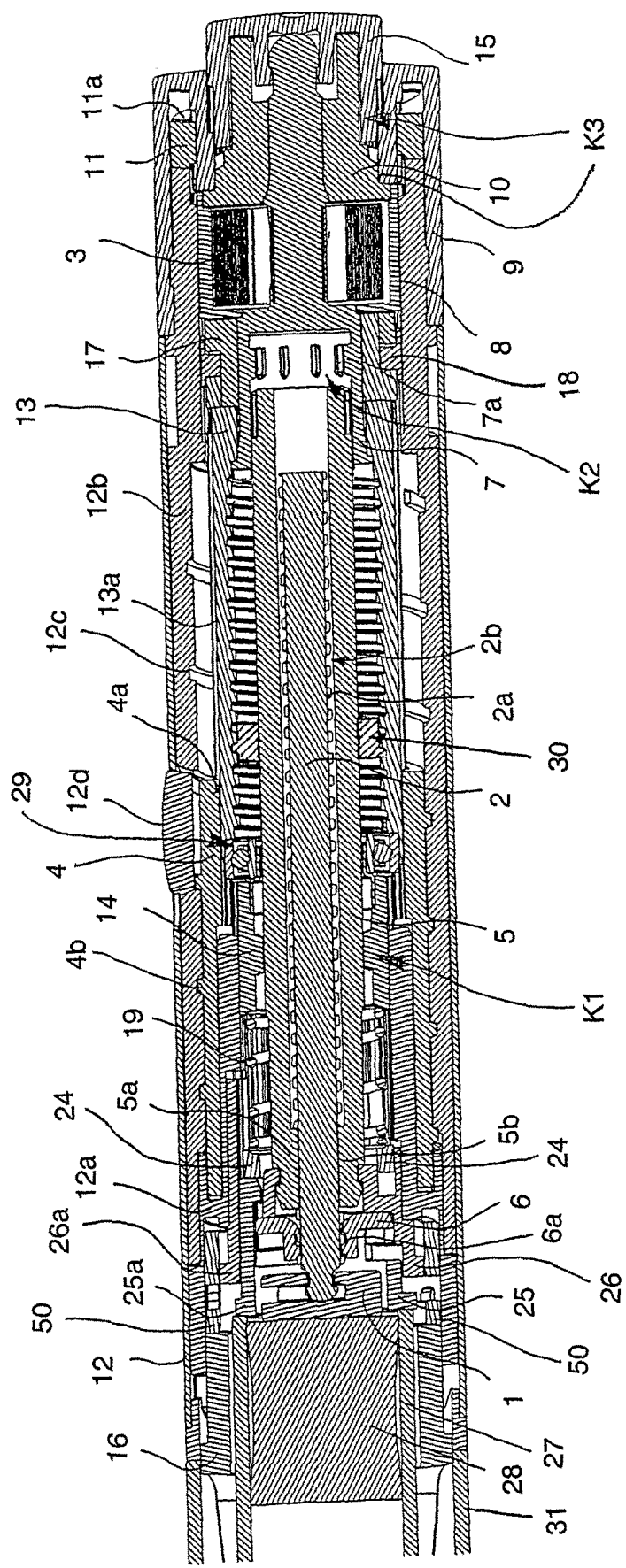
FIG. 1 is a cross-sectional view illustrating a proximal (rear) part of an embodiment of an injection device in accordance with the present invention.

The injection device illustrated in FIG. 1 comprises a drive unit, which, in some embodiments, can be used more than once, and a product container 27 connected to it, which is accommodated in a sleeve-shaped product container holder 16 which can be used multiple times, for example, and which can be secured to the drive unit with the aid of the product container holder 16. The product container 27 can be removed from the injection device after it is empty, disposed of and replaced with a new one. With a view to simplifying the manufacturing and assembly processes, the housing 12 is of a multi-part design comprising housing elements 12a, 12b connected to or inserted in it, although in principle, the housing could also comprise a single part. The product container 16 is attached to the drive unit by a bayonet fitting, which is formed by the housing 12, product container holder 16 and sleeve 50. The product container holder 16 is covered by a cap 31, which is fitted on the housing 12, and can be removed in preparation for using the injection device and then fitted back on it.

Figure 4:
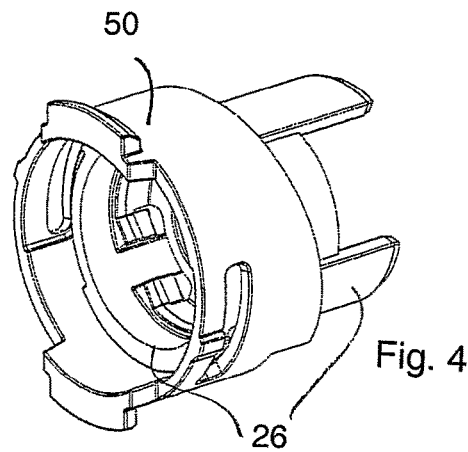
FIG. 4 is a perspective view of the bayonet sleeve illustrated in FIG. 3 with a locating element inserted in it.
Figure 5:
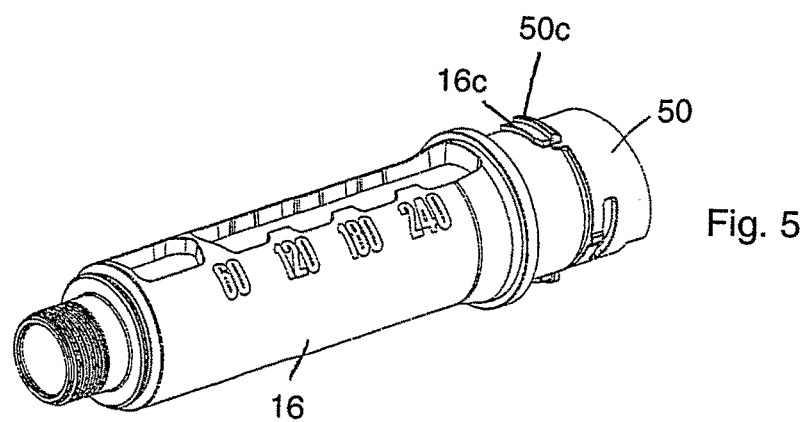
FIG. 5 is a perspective view of a bayonet sleeve and product container holder, which is moved axially into a fixed torque-transmitting engagement.

FIGS. 2 to 5 illustrate elements of the fixing device provided in the exemplary form of a bayonet fitting. The product container holder 16 has a cam 16c extending radially outwardly and at its proximal (rear) end face is designed so that it can be connected in a positive fit, i.e. in a fixed torque-transmitting fit, to the distal (forward) end face of the sleeve 50, as illustrated in FIG. 5 where housing part 12a has been omitted for illustration purposes. The sleeve 50 has at least one cam 50c extending radially outwardly, which forms a part of a cam (which may be thought of as comprising cam elements 16c, 50c) for the fixing device. The cam 50c locates or is positioned in a guide track 12e formed in the housing 12, e.g. in housing part 12a, which has at least one inclined surface 12g. When the sleeve 50 is moved in rotation, the sleeve 50 moves axially relative to the housing part 12a as well as moving in rotation, due to the locating cam 50c. As will be described below, the axial movement of the sleeve 50 results in various advantageous effects.

Figure 2:
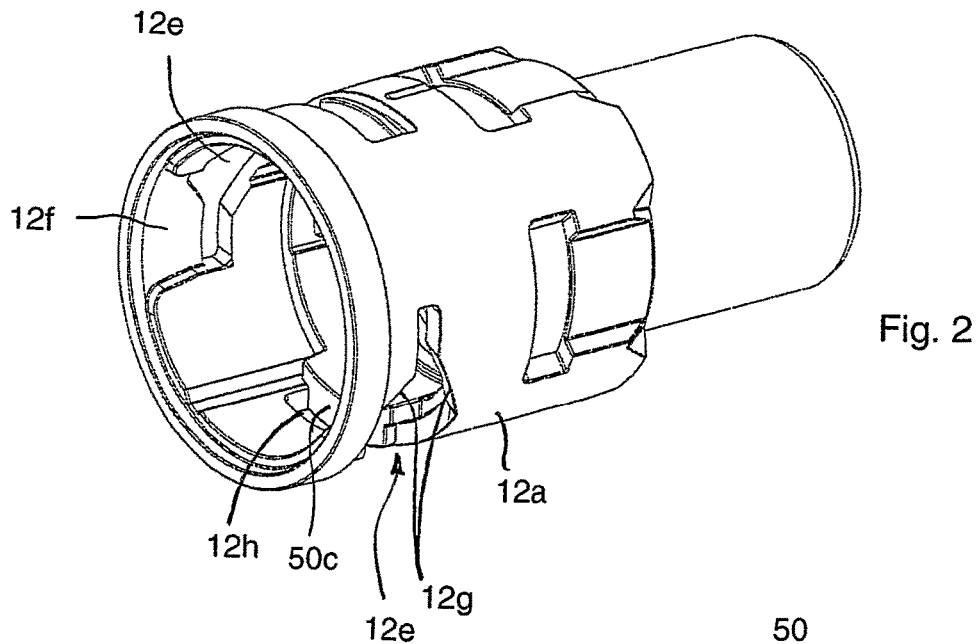
FIG. 2 is a perspective view of an embodiment of a housing part with a guide track for a bayonet lock and an inserted bayonet sleeve.
Figure 3:
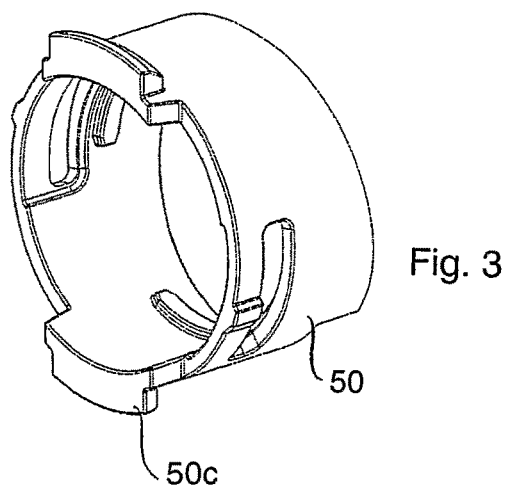
FIG. 3 is a perspective view of the bayonet sleeve illustrated in FIG. 2.

To fit the product container 27 on the drive unit, it may be introduced into the product container holder 16 via the proximal end. The product container holder 16 is then snap-fitted onto the sleeve 50 by an axial movement resulting in a fixed torque-transmitting fit (FIG. 5), so that the cams 16c are inserted through the opening 12f (FIG. 2) into the guide track 12e. FIG. 2 illustrates the bayonet fitting in a locked state without the product container holder 16. In an unlocked state in which the cams 50c are disposed in the region of, and axially flush with the openings 12f, the product container holder 16 can be push-fitted. The cams 16c and 50c then lie one against the other and form a common cam (FIG. 5). A rotation of the product container holder 16 causes the sleeve 50 to be driven. Due to the inclined faces 12g, the sleeve 50 and the product container holder 16 are also moved axially. At the end of the rotation, i.e. on reaching the locked position, the common cam (comprising cam elements 16c, 50c) is disposed in the region 12h of the guide track 12e in which the two cams 16c and 50c are axially clamped together by the sides of the guide track 12e. To this end, the axial width of the guide track in the region 12h is approximately as wide as that of the joint cams 16c, 50c.

As illustrated in FIG. 4, a guide sleeve 26 is accommodated in the sleeve 50, which may also be thought of and/or referred to as the bayonet sleeve. The guide sleeve 26 is connected to the housing 12 so that it can not rotate but can move axially and is connected to the bayonet sleeve 50 so that it can rotate but can not move axially. As a result, when the bayonet sleeve 50 is moved from the unlocked to the locked position and vice versa, the guide sleeve 26 effects a longitudinally guided movement relative to the housing 12.

As may be seen from FIG. 1, a threaded insert 6 is connected and/or latched to the guide sleeve 26 so that it can not rotate or move axially. The threaded insert 6 and guide sleeve 26 may be thought of and/or referred to as a locating element (comprising insert and sleeve elements 6, 26). The threaded insert 6 has an internal thread 6a in which the external thread 2a of an output element 2, which might also be called a plunger rod in this example, is guided so that when the output element 2 is rotated, it is guided by the internal thread 6a of the threaded insert 6 in the proximal direction or in the distal, i.e. opposite, direction, as it is screwed, depending on the direction of rotation.

On its external face, the output element 2 has a thread 2a, which is interrupted by two grooves 2b extending in the axial direction lying opposite one another on the circumference. A coupling sleeve 5 constituting part of a transmission (comprising elements 7, K2, 5) has two projections 5a, 5b directed radially inwardly lying opposite one another on its distal end which project into the grooves 2b of the output element 2. The coupling sleeve 5 is connected to the locating element so that it can rotate but is not able to move axially. Accordingly, the output element 2 is locked to prevent it from rotating relative to the coupling sleeve 5 but is able to move axially relative to the coupling sleeve 5 when it is rotated relative to the locating element. The coupling sleeve 5 is not able to move axially expect for when the product container 27 is being replaced.

A drive shaft 7 provided at the proximal end of the injection device and forming part of the transmission has teeth 7a extending radially inwardly which constitute a coupling element of the coupling K2. When operated, i.e. when an operating element 15 is pushed in the distal (forward or injection) direction, the drive shaft 7 and as a result also the teeth 7a are moved in the distal direction, as result of which the teeth 7a locate in the proximal end of the coupling sleeve 5 and establish a fixed torque-transmitting, positive connection.

A spring element or drive spring 3, which may be provided in the form of a helical spring or clock spring, is connected to the housing 12 by one end via a spring sleeve 8 on the external face of the spring 3. The spring sleeve 8 is prevented from rotating relative to the housing 12 but is able to move axially. At the other end, the drive spring 3 is connected to the drive shaft 7. As a result, energy stored in the spring 3 can be output as a rotating movement of the drive shaft 7 relative to the housing 12. To dispense a product, the energy of the spring element 3 is transmitted via the transmission element in the form of a rotating movement to the output element so that the latter is screwed relative to the locating element in the distal direction, i.e. in the dispensing direction, and pushes the plunger 28, causing the product to be dispensed from the product container 27.

To set a product dose to be administered, a user can rotate the dose setting element 9 provided in the form of a dose setting button, which is axially fixed relative to the housing 12. The dose setting element 9 is coupled with a coupling element 10 via the coupling K3 so that it is prevented from rotating. The coupling K3 is formed by webs or grooves or teeth of the dose setting button 9, which co-operate in a positive fit with webs or grooves or teeth of the coupling disc 10 to establish a coupling which can be released by a movement of the coupling element 10 in the distal direction. The coupling element 10 can be moved and thus released by operating the operating element 15. When in a state of not being operated, the coupling K3 is held in a coupled state and the coupling K2 in an uncoupled state by a spring element 19, which pushes the drive shaft 7 in the proximal (rear or rearward) direction. During the dose setting operation, the coupling K3 is coupled, i.e. a rotating movement of the dose setting button 9 is transmitted to the coupling element 10. The coupling element 10 is connected to the drive shaft 7 so that it can not move axially and can not rotate and could also be an integral part of the drive shaft 7. The rotating movement of the dose setting element 9 is not transmitted to the coupling sleeve 5 because the coupling K2 is uncoupled.

When the drive shaft 7 is rotated, the drive spring 3 connected to the drive shaft 7 is tensed. To prevent the dose setting button 9 from being turned back due to the drive spring 3 as it is tensed during the setting operation, a ratchet 11 or a ratchet mechanism, which may comprise a ratchet spring 11a, e.g. for clamping retaining elements, may be provided between the housing 12 of the injection device, the components of which might, for example, be a mechanical holder 12a and a mechanical holder 12b and the dose setting button 9. The ratchet mechanism may be designed so that a rotation and/or a tensing of the drive spring 3 is possible in only one direction. In some preferred embodiments, however, the ratchet mechanism is designed so that the rotating action is possible in both directions, e.g. tensing and relaxing of the drive spring 3. Due to the fact of being able to rotate in both directions, a product dose can be both increased and reduced when setting the product dose. A currently set product dose can be read through the window 12d of a display barrel 4.

The rotating movement of the drive shaft 7 is also transmitted to the threaded sleeve 13, which is connected to the drive shaft 7 so that it is not able to move axially or rotate and may also be an integral part of it. The threaded sleeve 13 has at least one groove on its external circumference 13a in which at least one web 4a of the display barrel 4 locates so that a rotating movement of the threaded sleeve 13 is transmitted to the display barrel 4 by the anti-rotation coupling, permitting an axial relative movement between the display barrel 4 and threaded sleeve 13. The display barrel 4 has a thread 4b on its external face which locates in an internal thread 12c of the housing part 12b so that the display barrel 4 is moved due to a rotating movement in the axial direction relative to the housing 12, e.g. in the distal direction. In some preferred embodiments, the display barrel 4 moves in the distal direction of the injection device (towards the left in FIG. 1) during the process of setting and priming the dose by rotating the dose setting button 9. A marking may be provided on the external face of the display barrel 4, such as print, a dose display or a scale, which can be read through an opening or a window 12d in the housing 12b of the injection device, and the marking of the display barrel 4 is moved relative to the window 12d. The display barrel 4 has a rotation stop on its distal end acting in the circumferential direction which moves into an abutting contact with a co-operating complementary stop disposed on the housing part 12a on reaching the maximum dose. The complementary stop is formed by a terminal end of an annular gap of the housing part 12a. An advantage of using a stop which acts in the circumferential direction rather than an axial stop is that the forces acting on the stop are weaker. The display barrel 4 also has another rotation stop on its proximal end acting in the circumferential direction, which moves into an abutting contact with a co-operating complementary stop on the housing 12b on reaching a minimum dose. The complementary stop is formed by the proximal end of the thread 12c.

Figure 14:
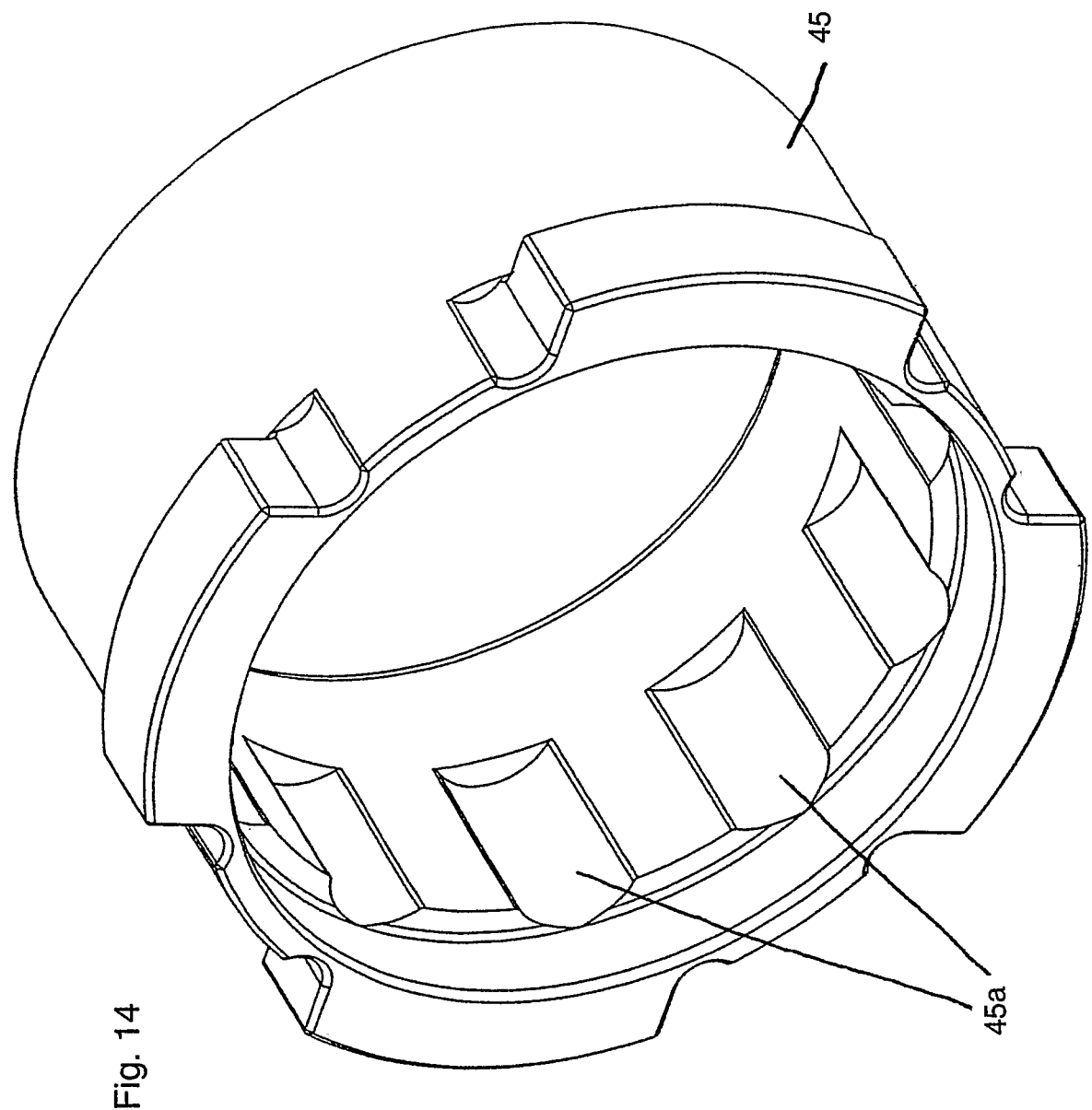
FIG. 14 is a perspective view of a brake housing from FIG. 13.

Once the dose has been set and the drive spring 3 primed by rotating the dose setting button 9, the setting operation is complete. In some preferred embodiments, the dose is primed as the spring 3 is tensed. To correct or adjust the dose, the dose setting button 9 simply has to be rotated in the opposite direction, e.g. to reduce a dose which might have been set too high. In some embodiments, the ratchet 11 may be designed as illustrated in FIGS. 14 and 15 of patent application PCT/CH2007/000243 and/or US Publication 2009/0254035, the teachings of which are incorporated herein by reference.

During the dispensing process, which is triggered by depressing the push button 15, the display barrel 4 is rotated back in the opposite direction and is moved back in the proximal direction due to the thread engagement with the internal thread 12c of the injection device (to the right in FIG. 1). As this happens, it reaches a stop of the display barrel 4 acting in the circumferential direction on the housing of the injection device, e.g. on the housing part 12b. In an unbraked dispensing movement in which the threaded rod 2 is moved in the distal direction without any opposing force, e.g. when no product container has been inserted, this operation may result in too high a strain and, in an extreme situation, deformation or even damage to the display barrel 4 or co-operating part 12b. A brake mechanism (e.g. comprising brake elements, e.g. shoe halves and disc 17, 18) acting on the driving movement is therefore provided, which will be described below.

The coupling K1, comprising the coupling element acting as a lock sleeve 14 and the coupling sleeve 5, is used to couple the coupling sleeve 5 with the housing 12 so that it can not rotate in specific operating modes or to release it to permit a rotation relative to the housing 12. The coupling K1 is uncoupled when the product container 27 is being replaced to enable the output element 2 to be pushed back or screwed in the proximal direction again and to enable the output element 2 to be screwed in the distal direction while product is being dispensed. The coupling K1 is coupled when the product container is attached to the drive unit and the operating element 15 is not being operated. The coupling K1 is provided in the form of teeth on the external face of the coupling sleeve 5, which mesh in teeth on the internal face of the lock sleeve 14. As a result, the coupling sleeve 5 is prevented from rotating relative to the lock sleeve 14. The lock sleeve 14 is mounted in the injection device so that it can not rotate but can move axially relative to the housing 12 and the coupling sleeve 5.

During a dispensing operation, the threaded sleeve 13 is moved in the distal (forward or injection or delivery) direction by operating the operating element 15. As this happens, the threaded sleeve 13 pushes on the bearing 29, which is provided in the form of a ball bearing in this example but may also be a simple slide bearing, so that the bearing 29 pushes against the lock sleeve 14, thereby moving it in the distal direction for a dispensing operation, and holds it in a distal position during a dispensing operation. The coupling element 14 is therefore disposed distally of the projections of the coupling sleeve 5 for the coupling K1. As a result, the coupling K1 remains uncoupled for the duration of the dispensing operation.

When the operating element 15 is operated, the couplings K1, K2 and K3 operate as follows. By depressing the push button 15 seated on the coupling element 10 and/or drive shaft 7, the coupling element 10 is pushed in the distal direction together with the push button 15 and the drive shaft 7. As a result, the coupling K2 is coupled so that the drive shaft 7 is prevented from rotating relative to the coupling sleeve 5. The coupling K1 is then uncoupled due to the movement of the lock sleeve 14, against which the threaded sleeve 13 connected to the drive shaft 7 pushes via the axially displaceable bearing 29. Alternatively, the couplings K1 and K2 may be connected in the reverse sequence.

Once K2 is coupled and K1 is uncoupled, the coupling K3 is also uncoupled due to the movement of the coupling element 10 relative to the dose setting button 9. The coupling element 10, which is connected to the drive shaft 7, is able to rotate relative to the housing 12 once the coupling K3 is uncoupled. The energy or force stored in the drive spring 3 during priming can be transmitted to the drive shaft 7. Accordingly, a torque is applied to the drive shaft 7, which is transmitted by the coupled coupling K2 to the coupling sleeve 5, which rotates in unison with the drive shaft 7 and transmits this rotating movement to the output element 2, which is coupled with the coupling sleeve 5 so that it can not rotate. The output element 2, provided in the form of a threaded rod in this example, converts the rotating movement into an axial movement in the distal direction due to the thread engagement 2a, 6a with the locating element (comprising elements 6, 26), so that the flange 1 provided on the distal end of the threaded rod 2, which may also be construed as part of the output element, is moved in the distal direction of the injection device.

Since, during the product dispensing operation, the threaded sleeve 13 moves in the direction opposite that in which it moves during priming, the display barrel 4 likewise moves in the direction opposite that of the priming operation.

In the normal situation, i.e. when a pre-set product dose has been fully dispensed, the dispensing operation and the movement of the output element 2 in the distal direction continues until the display barrel 4 makes contact with the above-mentioned stop acting in the circumferential direction. In some embodiments, this happens when the value which can be read through the window 12d has been rotated back to 0.

In the situation in which the user of the device releases the operating element 15 as the product is being dispensed, the couplings couple in the order which is the reverse of that in which they uncoupled or coupled during operation. The product dispensing operation is interrupted, as a result of which the value may be seen through the window 12d represents the amount still to be dispensed had the pre-set dose been fully dispensed. The product dispensing operation can be continued by depressing the operating element 15 again, and dispensing can be stopped again by releasing the operating element 15 or the user can wait until the product has been fully dispensed.

In the situation in which the product container contains less product than the maximum dose indicated on the display barrel, the injection device based on this example has an additional device for limiting the maximum dose which can be set for the last time, to prevent the possibility of a bigger product dose being set than that which is still in the container. To this end, a traveller 30 is provided, which at least partially surrounds the coupling sleeve 5 and locates with the coupling sleeve 5 in such a way that the traveller 30 is not able to rotate relative to the coupling sleeve 5 but is able to move axially. The traveller 30 also locates or is positioned by a thread on its external circumference that engages with an internal thread of the threaded sleeve 13. This arrangement causes an axial movement of the traveller 30 when there is a relative rotation between the threaded sleeve 13 and coupling sleeve 5, and when there is no relative rotation the traveller 30 does not effect an axial movement. When setting a product dose, the threaded sleeve 13 turns relative to the coupling sleeve 5 so that the traveller 30 moves in the proximal direction. During dispensing, on the other hand, no relative movement takes place between the coupling sleeve 5 and threaded sleeve 13 due to the coupled engagement of the coupling K2. Accordingly, the traveller does not move. After setting doses and dispensing product several times, the traveller 30 moves into an abutting contact with the drive shaft 7, so that it is no longer possible to increase the dose, even if the display would actually permit this.

The user can replace the product container 27 with a new one. To this end, the product container holder 16 may be removed by rotating the drive unit relative to the housing 12. As the product container 27 is moved from the secured position into the non-secured position, e.g. as the bayonet fitting is released, the locating element is moved together with the output element 2 and the coupling sleeve 5 in the distal direction relative to the housing 12 and to the coupling element 14, thereby releasing the coupling K1. The projections of the coupling sleeve 5 pointing radially outwardly to establish the coupling K1 are now disposed distally of the coupling element 14. The output element 2 can now be screwed into the drive unit with a relatively slight force acting in the proximal direction because the thread of the output element is not retained by friction. As the output element 2 is screwed back, the coupling sleeve 5 is turned relative to the threaded sleeve 13 and so in the direction opposite that during product dispensing, causing the traveller 30 to be pushed back in the distal direction again. The screwing-back operation may take place against the force of a spring element, at least across a part of the total distance, which tries to push the output element in the distal direction, for example. The spring element may act or be disposed between the output element 2 and the drive shaft 7 for example. Other possible spring elements will be described below specifically with reference to FIG. 6. It is generally preferred if the force of such a spring element is weaker than the force needed to produce an interaction via the plunger from the output element 2 onto the product.

Also during the process of removing the product container 27, the retaining element 25 used to secure the product container 27 in the product container holder 16 is pushed in the distal direction by the spring 19 until it makes contact with the locating element 6, 26. This contact prevents the spring 19 from fully relaxing when the product container 27 is removed. This is of advantage because the spring 19 should be able to apply sufficient force to hold the coupling K3 in a coupled engagement even when a product container 27 has been removed.

Figure 6:
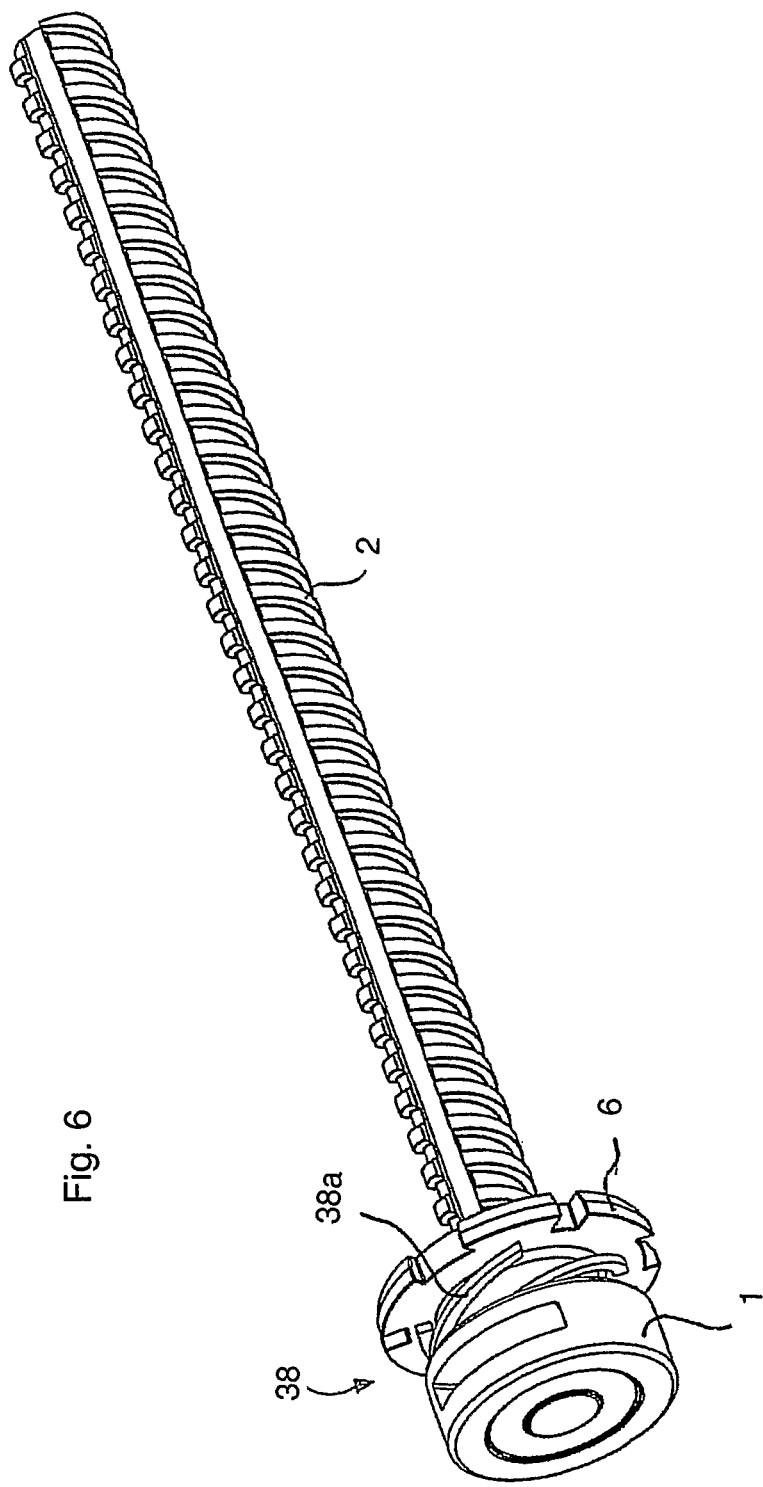
FIG. 6 is a perspective view of an output element with a flange and spring element.

By virtue of another aspect, a spring-mounted flange may be used, as illustrated in FIG. 6 for example.

After replacing the product container 27, e.g. an ampoule, capped vial or the like, the user is prompted to proceed with priming, as may be described in operating instructions. This is useful on the one hand because there may be air in the product container 27 and on the other hand because the output element 2 may have been previously pushed fully into the drive unit and a certain amount of clearance may have been created between the plunger 28 and the flange 1 due to the different level to which the product container 27 is filled.

FIG. 6 illustrates an output element 2 with a flange 1 attached to its front or distal end, which is non-displaceably connected to the threaded rod. Disposed between the flange 1 and the threaded insert 6 illustrated in FIG. 6 is a spring element 38, which may be provided in the form of resilient arms 38a extending out at an angle, for example. These resilient arms 38a may be secured to the flange 1 or/and to the threaded insert 6. Another option would be to injection mold a suitable elastomer onto the flange 1 or/and onto the threaded insert 6. After a new product container 27 has been inserted, a clearance may occur between the flange 1 and the plunger 28, which may be attributable to a difference in the level to which product containers 27 have been filled when full, given that they have a certain tolerance.

After pushing in the flange 1 connected to the threaded rod 2, the flange 1 based on the embodiment illustrated in FIG. 1 lies directly against the threaded insert 6.

In the embodiment illustrated in FIG. 6, the at least one spring element 38 has pushed the flange 1 away from the threaded insert 6 in the distal direction by a predefined distance. This means that when a product container 27 has been inserted or while a product container 27 is being inserted, the flange 1 will move into contact with the proximal end of the plunger 28, even if the plunger 28 is pushed into the product container 27 by differing distances caused by manufacturing tolerances of different product containers. Conventional means for eliminating the clearance between the flange 1 and plunger 28 are therefore no longer absolutely necessary and may even be dispensed with, for example.

As may be seen from FIG. 1, the injection device, e.g. the drive unit, comprises a brake (which may be thought of as comprising brake elements or components 17, 18) which decelerates a rotating part, in this example the transmission element or/and the driving movement. If conventional injection devices are used incorrectly, i.e. if no product container has been inserted, but the device is nevertheless operated, there is a risk of placing too high a strain on or even damaging the components of the injection device. When a product container 27 is inserted, the forces and movements which occur are damped by the viscosity of the product during the product dispensing operation. In the absence of a product container, there is no such damping effect. It is the brake in accordance with the present invention which is used for this purpose, thereby preventing excessive strain.

Figure 7A:
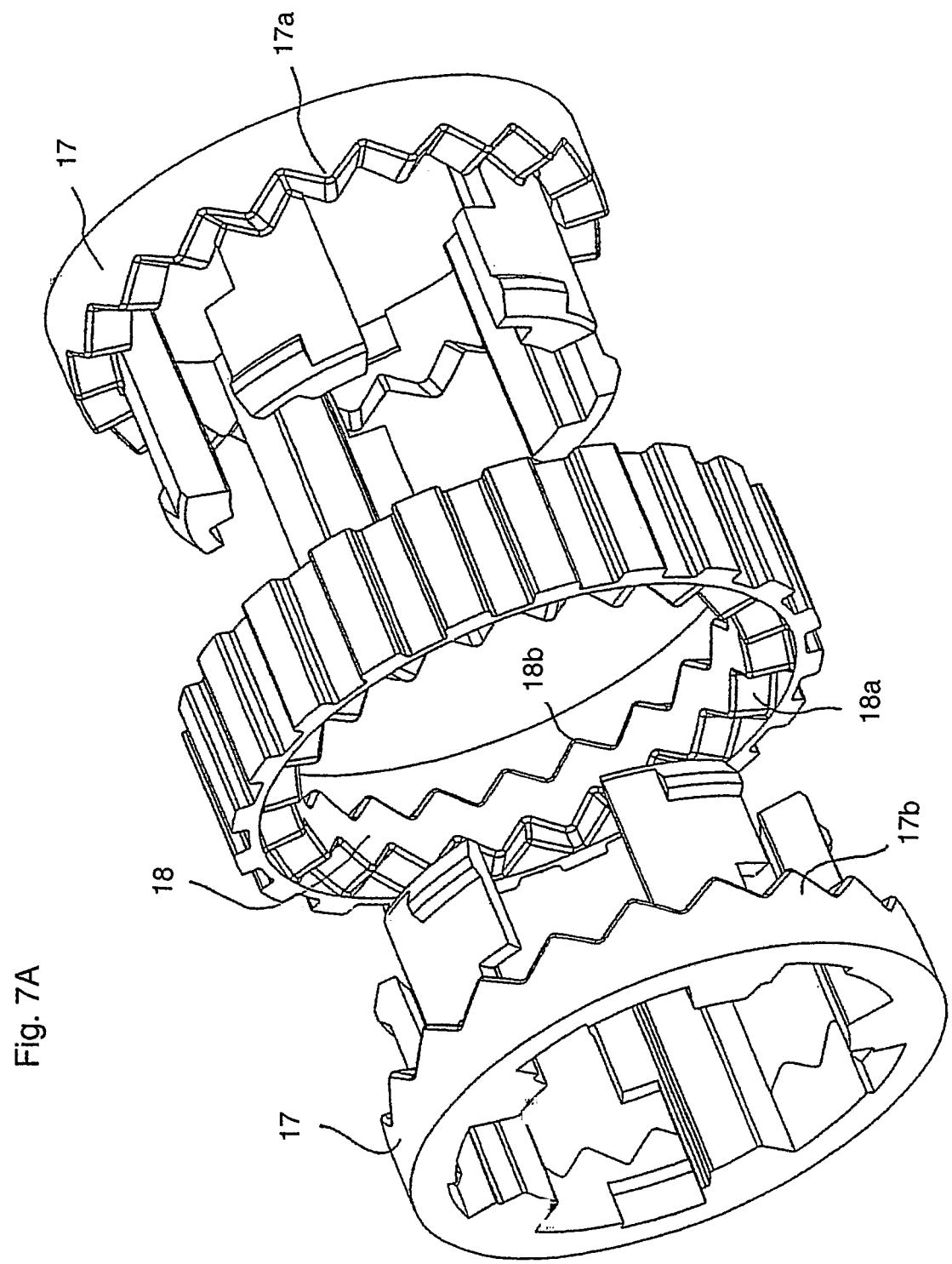
Figure 8:
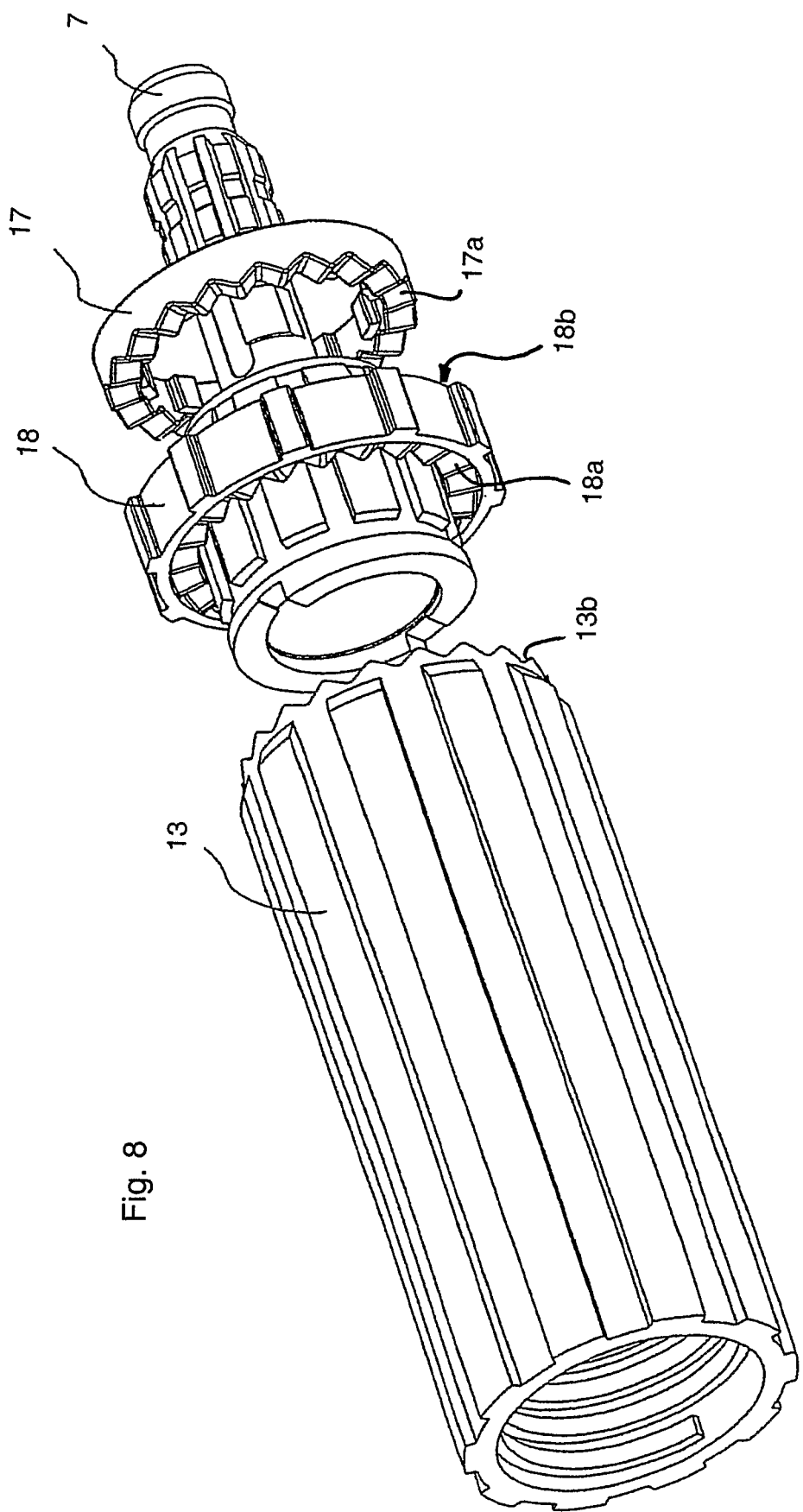
FIG. 8 is a perspective, exploded diagram of another embodiment of a brake mechanism in accordance with the present invention.

FIGS. 7A, 7B and 8 are diagrams on a larger scale illustrating embodiments of a brake mechanism suitable for the device illustrated in FIG. 1, e.g. a first and second embodiment, respectively, each of which operates in a similar manner. The first embodiment illustrated in FIGS. 7A, 7B has two brake shoe halves 17 latched to one another so that they can not rotate and so that they can also not move axially, which have profiled portions directed toward one another, between which an annular gap is formed in which a brake disc 18 is accommodated. The annular gap is of a defined width and, in an alternative arrangement, the brake shoe halves could move axially relative to one another. The brake shoe 17 could be of an integral design. The brake disc 18 is accommodated so that it can not rotate relative to the housing 12 but can move axially, due to the profiled external circumferential surface of the brake disc locating in a profiled inner circumferential surface of the housing part 12b. At least one brake shoe half 17 or the entire brake shoe is mounted at least so that it can not rotate in the drive train or transmission element. The sleeve-shaped brake shoe 17 has projections pointing radially inwardly, which locate in a matching profile of the drive sleeve 7. The brake disc 18 is able to move between the brake shoe halves 17. The brake disc 18 is mounted so that it can not rotate, e.g. is guided in a groove, and so that it is able to move axially in the injection device or housing part 12b. The brake disc 18 is toothed on the top and bottom face with teeth 18a, 18b on the end face projecting circumferentially in both directions and having an identical or different tooth height ZH, and is mounted or displaceably clamped between the threaded sleeve 13 and the brake shoe 17, e.g. with a small clearance of approximately a tooth size or tooth height ZH or bigger, the latter having co-operating complementary teeth 13b respectively 17a, e.g. with a corresponding or identical tooth height ZH.

Due to the fixed torque-transmitting connection between the transmission element (which, again, may be thought of and/or referred to as comprising elements 7, K2, 5) during a dispensing operation or when what may be thought of and/or referred to as "firing blank," i.e. when no product container has been inserted, the brake shoe 17 is moved in rotation relative to the brake disc 18. When this happens, the disposition of the brake shoe teeth 17a, 17b ensure that the brake disc 18 oscillates axially between the threaded sleeve 13 and the brake shoe 17. As a result, the distal teeth 18a and proximal teeth 18b of the brake disc 18 move alternately into contact with the co-operating complementary teeth 17b and 17a. Due to one or more of the resultant friction, elastic deformation and the oscillating mass, a corresponding loss occurs, thereby limiting the maximum angular speed w of the rotating parts 13 and 17.

The embodiment illustrated in FIG. 8 operates on a similar principle, the difference being that one of the two brake shoe halves and/or its end-face tooth profile is formed by the transmission element or the threaded sleeve 13 connected to the transmission element so that it cannot rotate. A fixed, defined distance may be provided between the profiles 17a and 13b, or alternatively a variable distance, because the brake shoe half 17 is able to move axially relative to the threaded sleeve 13. Due to the spring 19, the profiles 13b and 17a can be pushed toward one another so that they move into a meshing contact with the profiles 18a and 18b.

Figure 9:
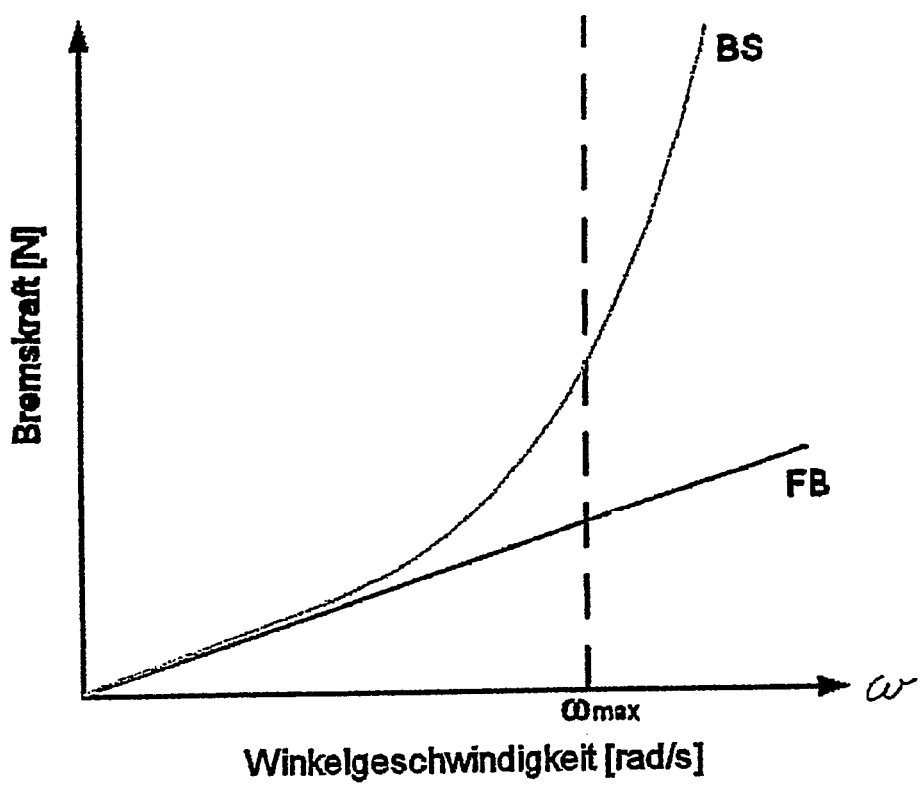
FIG. 9 is a diagram schematically plotting braking force as a function of angular speed.

Due to the vibration or oscillation of the brake disc 18 between the threaded sleeve 13 and brake shoe 18 which increases with the angular velocity ω, the braking force increases disproportionately as the angular velocity ω increases, so that the curve BS of braking forces schematically illustrated in FIG. 9 can be achieved.

FIG. 9 is a schematic illustration plotting the curve of the braking force which can be achieved by a brake mechanism in accordance with the present invention, from which it may be seen that the braking force rises to an increasing degree with the angular or rotational velocity ω. In some preferred embodiments, the braking force is relatively low or zero up to the maximum permissible angular velocity $\omega_{max}$ and rises sharply with effect from the maximum permissible angular velocity $\omega_{max}$.

Figure 10:
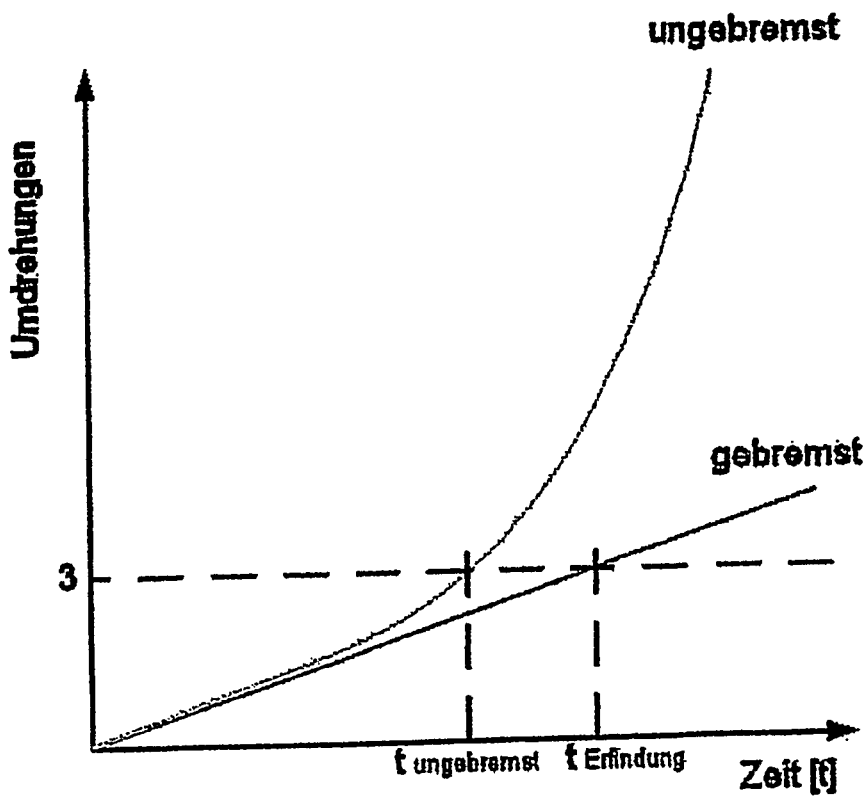
FIG. 10 is a diagram illustrating braking action as a function of time.

FIG. 10 illustrates the angle of rotation of the display barrel 4 as a function of time, which is able to effect three full revolutions (3×360°) in the embodiments illustrated as an example. As may be seen from FIG. 10, the display barrel 4 has completed three full revolutions after the time $t_{non-braked}$, which is shorter than the time $t_{invention}$ in the case of a decelerated rotating movement of the display barrel 4 during which the angle of rotation increases linearly as a function of time.

Due to the braking force generated by the oscillating brake disc 18, the maximum possible angular velocity $\omega_{max}$ of a dispensing movement can be reduced or limited so that the backward-rotating display barrel 4 is able to move into an abutting contact with the stop acting in the circumferential direction or the housing part 12b at only a maximum speed predefined by the brake. If the brake is designed accordingly, the maximum possible contact speed of the display barrel 4 is so low that there is little chance of deformation or damage occurring due to the impact. Other brake mechanisms may also be used as an alternative to a brake disc 18 oscillating between the threaded sleeve 13 and brake shoe 17.

For example, as an alternative or in addition, the brake may be based on another embodiment in the form of a centrifugal brake as illustrated in FIG. 12. In this case outwardly displaceable brake shoes 41 are mounted on the transmission element or/and the drive shaft 7 and/or another part which rotates with the drive shaft 7, for example the coupling element 10, the threaded sleeve 13 or the display barrel 4, which have a mass and which effect the same rotation as the rotating part. The brake shoes 41 may, but need not necessarily, be inwardly or outwardly biased by a spring. The brake shoes may be pivoted or moved radially outwardly by the centrifugal force to move into a braking engagement with a sleeve 42, for example the housing 12. In this embodiment, pins 40 or fasteners extending radially outwardly are provided, the ends of which are provided with brake pads 41 biased by the spring, for example. When the rotation speed of the non-braked or only partially braked rotating element is sufficiently high, the brake pads 41 are moved radially outwardly by the centrifugal force, optionally also assisted by the spring-biased support, and can move into contact with an outer static sleeve 42, thereby producing the desired braking effect due to friction. The outer static sleeve may also be formed by the housing 12 or housing part 12b.

Figure 11A:
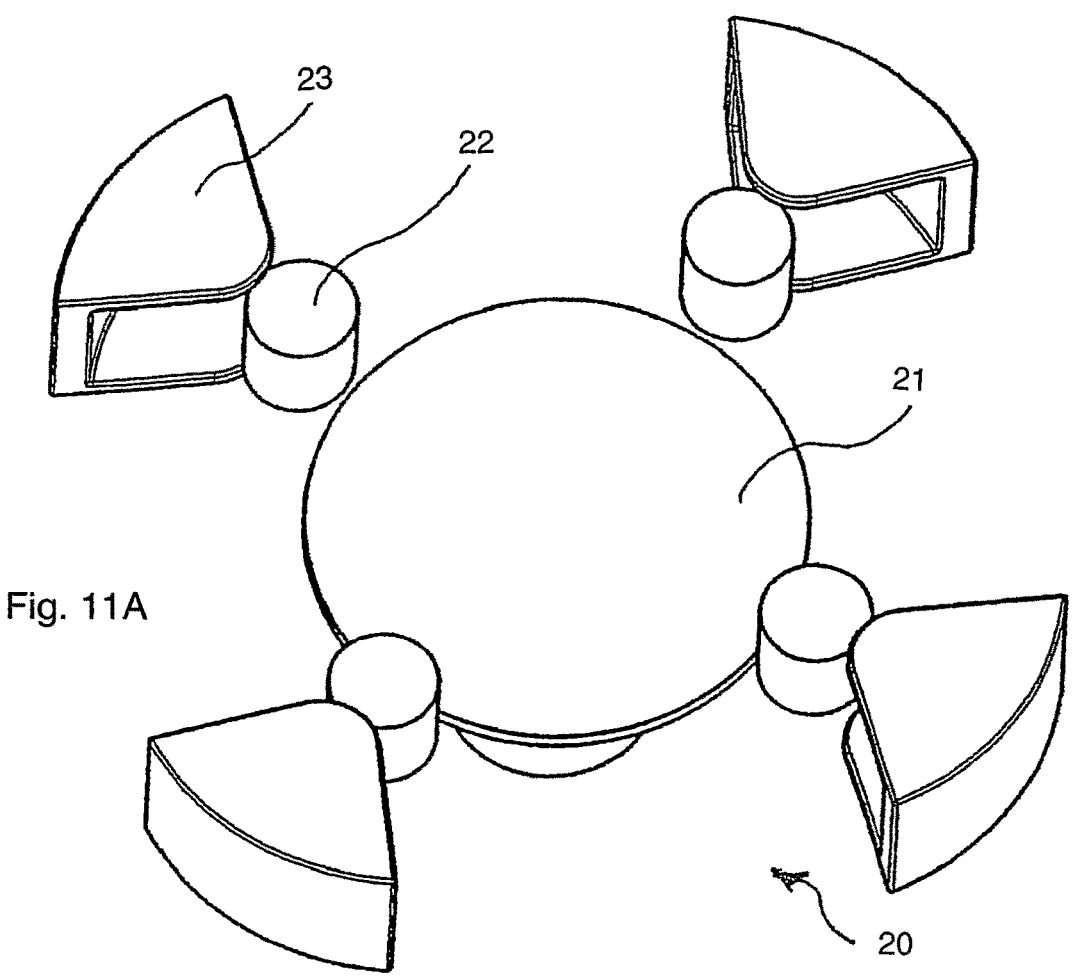
FIGS. 11A and 11B are, respectively, an exploded view and a perspective view of an embodiment of a brake mechanism in accordance with the present invention operating on the principle of an eddy current brake.
Figure 11B:
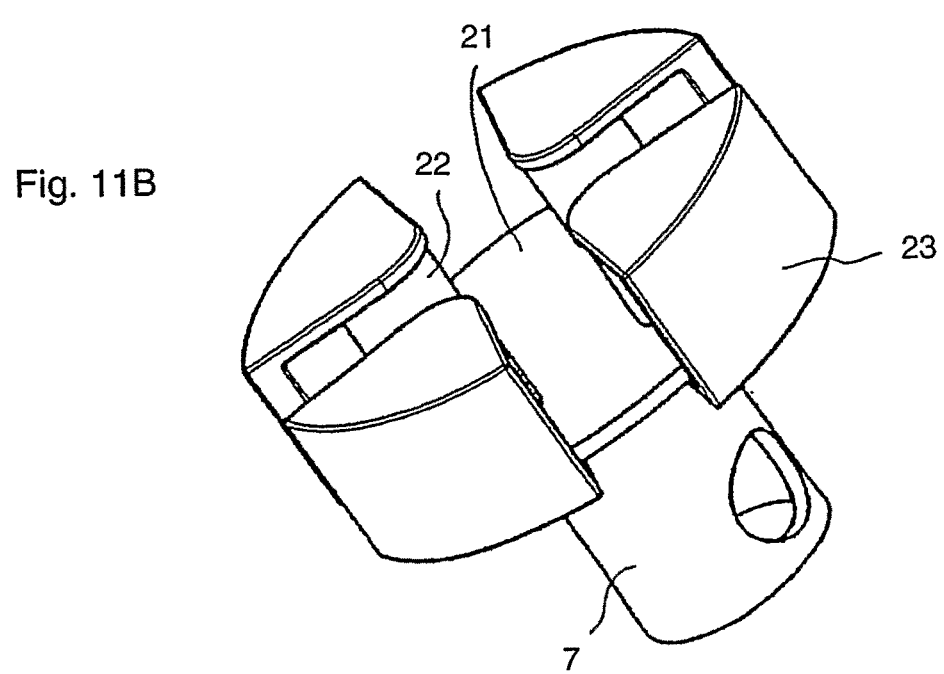

In another embodiment illustrated in FIGS. 11A and 11B, the brake may be provided in the form of an eddy current brake 20, in which case a brake disc 21 may be connected to a rotating part which has to be decelerated, for example the transmission element, drive shaft 7, threaded sleeve 13 or display barrel 4, and the elements interacting with the brake disc may be connected to the housing or an element fixedly disposed on the housing or to an element rotating relative to the brake disc.

In some preferred embodiments, the brake disc 21 is made from a good electrical conductor, such as pure aluminium or copper, for example. Rare earth alloys may be used as the material for the axially magnetised magnets 22, neodymium for example. The permanent magnetic field may be linked by a magnet yoke 23 made from iron to the air gap, where it extends through the brake disc 21 as vertically as possible. The braking force is created by the surface and flow density in the air gap and the rated current in the brake disc 21, for which purpose the surface should be as large as possible, the air gap should be as small as possible and the disc thickness should be as big as possible. The braking torque occurs over the averaged radius (working radius). Brakes may be designed with several magnet systems which act on a disc 21.

The usual approximation calculations are used to calculate the current density, braking power and hence braking torque of an eddy current brake. Leaving aside the effect of the air gap, it is assumed that there will be a standard cylindrical magnetic flow and it is stipulated as a condition that the pole diameter should be sufficiently small compared with the radius of the disc 21. At high speeds, the approximation is inaccurate, among other reasons because the magnetic fields caused by the eddy currents cause a not inconsiderable feedback and hence non-linearity.

In some preferred embodiments, the magnets 22 and the magnet yoke 23 are connected to the housing 12 of the injection device or the housing part 12b or another non-rotating part to be able to generate the desired eddy current braking effect of the brake disc 21.

Figure 13:
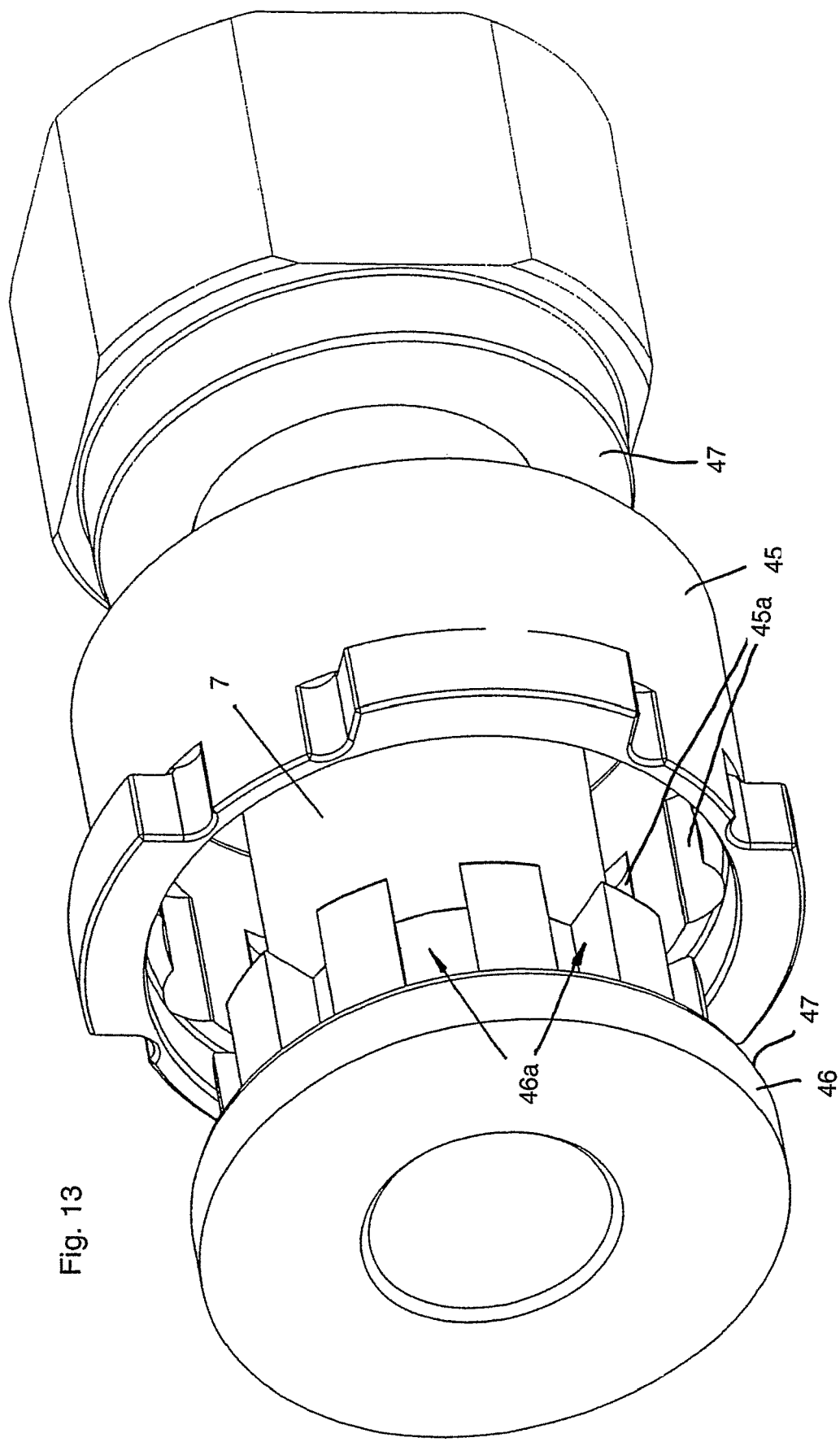
FIG. 13 is an exploded view of another embodiment of a brake mechanism in accordance with the present invention operating on the principle of a fluidic brake.

In another embodiment illustrated in FIGS. 13 and 14, the brake may be provided in the form of a fluidic or hydrodynamic brake. If a standard fluid is used as the braking medium, the linear braking curve FB indicated in FIG. 4 can be obtained for the eddy current brake. However, if the intention is to achieve a braking force which rises more sharply as a function of angular velocity ω, so-called non-Newtonian fluids may be used, as a result of which, unlike a Newtonian fluid, the viscosity does not remain constant but increases when a shearing force acting on the fluid is increased, which is the case as the speed increases. These are what are known as anomalous viscous fluids.

In the case of the fluidic brake, the braking force is generated by two fluid surfaces moving against one another. In particular, the braking force is generated by a fluid volume which is sheared by a relative movement. The shearing stresses which occur during such movements correspond to the braking force. The volume is provided in the form of a chamber split into two parts 45a, 46a, in which the fluid is disposed. One chamber part 46a is disposed in a rotating part 46 and the other chamber 45a is disposed in a part 45 relative to which the rotating part 46 is able to rotate. The part 46 may be connected so as to rotate in unison with the drive shaft 7 or to the transmission element or another part which rotates when product is being dispensed. The part 45 rotates in unison with at least the housing 12 or a stationary part on the housing. Furthermore, the part 45 may be able to move axially or may be axially immobile relative to the housing 12. The sleeve-shaped part 45 may be thought of and/or referred to as a brake housing and the part 46 mounted in the sleeve 45 as a brake shaft. When the brake is in the assembled state, the fluid chamber halves 46a distributed axially around the external circumference of the brake shaft are axially on a level with the fluid chamber halves 45a distributed around the internal circumference of the brake housing. More, the same number or fewer fluid chamber halves 45a may be provided than 46a. In the assembled state, a slim gap is disposed between the internal diameter of the brake housing 45 and the external diameter of the brake shaft 46 in the region of each of the fluid chamber halves 45a, 46a, which may be dimensioned so that fluid is conveyed into the gap or no fluid or virtually no fluid is conveyed into the gap when the brake shaft 46 is rotating relative to the brake housing 45. The brake housing 45 may be axially sealed at both ends with sliding seal elements 47 so that no fluid is able to escape from the brake. The seal elements 47 may be provided in the form of a lid. The lid may be provided as a separate part or serve as the coupling shaft, for example.

Embodiments of the present invention, including preferred embodiments, have been presented for the purpose of illustration and description. They are not intended to be exhaustive or to limit the invention to the precise forms and steps disclosed. The embodiments were chosen and described to illustrate the principles of the invention and the practical application thereof, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. An injection device for dispensing a product, the injection device comprising:
   a. a housing accommodating a drive unit;
   b. a product container holder configured for accommodating a product container, wherein a plunger is moveably accommodated in the product container;
   c. a plunger rod operatively connectable to a coupling sleeve of the drive unit and configured to move in and counter to a dispensing direction, wherein movement by the plunger rod in a dispensing operation causes the product to be dispensed from the product container, wherein the plunger rod includes a freely rotatable but axially fixed flange on a distal end of the plunger rod; and
   d. a locking element comprising teeth on an internal face, the locking element configured to be moved for the dispensing operation,
      wherein when the product container holder is secured to the drive unit and while a product dose is set, the teeth of the locking element are meshed with teeth on an external face of the coupling sleeve such that a movement of the plunger rod is blocked, and
      wherein when the product container holder is not secured to the drive unit, the plunger rod is permitted to be pushed back or screwed in a proximal direction and the teeth of the locking element are not meshed with the teeth of the coupling sleeve.

2. The injection device according to claim 1, further comprising a display barrel comprising an external thread configured to locate in an internal thread of the housing such that the display barrel is moved by a rotating movement in an axial direction relative to the housing.

3. The injection device according to claim 2, wherein the display barrel further comprises a first rotational stop acting in a circumferential direction, wherein the first rotational stop moves into an abutting contact with a co-operating complementary stop disposed on the housing upon reaching a maximum dose.

4. The injection device according to claim 3, wherein the complementary stop is defined by a terminal end of an annular gap of the housing.

5. The injection device according to claim 3, wherein the display barrel further comprises a second rotational stop acting in the circumferential direction, wherein the second rotational stop moves into an abutting contact with another co-operating complementary stop disposed on the housing upon reaching a minimum dose.

6. The injection device according to claim 5, wherein the another co-operating complementary stop is defined by a proximal end of the internal thread of the housing.

7. The injection device according to claim 1, further comprising a rotationally and axially fixed insert comprising an internal thread which guides an external thread of the plunger rod.

8. The injection device according to claim 1, further comprising:
   a drive shaft comprising teeth; and
   an axially displaceable operating element operable by a user,
   wherein a displacement of the operating element in a distal direction causes the drive shaft to move in the distal direction such that the teeth of the drive shaft locate in the coupling sleeve, thereby coupling the drive shaft and the coupling sleeve and preventing relative rotation between the drive shaft and the coupling sleeve.

9. The injection device according to claim 1, further comprising a device for limiting a maximum dose which can be set beyond an amount of the product remaining in the product container.

10. The injection device according to claim 9, wherein the device for limiting the maximum dose comprises a traveler at least partially surrounding the coupling sleeve.

* * * * *